United States Patent [19]
Römhild

[11] Patent Number: 6,142,856
[45] Date of Patent: Nov. 7, 2000

[54] SHARPENING DEVICE FOR DENTAL INSTRUMENTS

[75] Inventor: Ludwig Römhild, Berchtesgaden, Germany

[73] Assignee: Hawe Neos Dental Dr. H. v. Weissenfluh AG, Bioggio, Switzerland

[21] Appl. No.: 09/199,458

[22] Filed: Nov. 25, 1998

[30] Foreign Application Priority Data

Dec. 1, 1997 [EP] European Pat. Off. ............ 97810935
Apr. 17, 1998 [EP] European Pat. Off. ............ 98810336

[51] Int. Cl.⁷ .................................................. B24B 7/00
[52] U.S. Cl. ........................ 451/279; 451/280; 451/387
[58] Field of Search .................................... 451/278, 279, 451/280, 387, 405

[56] References Cited

U.S. PATENT DOCUMENTS

| | | | |
|---|---|---|---|
| 3,902,283 | 9/1975 | Bean | 451/279 X |
| 4,637,775 | 1/1987 | Kato | 451/279 X |
| 5,058,324 | 10/1991 | Snellen | 451/279 X |
| 5,070,654 | 12/1991 | Manqvist | 451/279 X |
| 5,297,362 | 3/1994 | Wykoff | 451/279 |

FOREIGN PATENT DOCUMENTS

| | | |
|---|---|---|
| 307740 | 3/1989 | European Pat. Off. . |
| 4307679 | 8/1993 | Germany . |
| 92/09403 | 6/1992 | WIPO . |

*Primary Examiner*—Timothy V. Eley
*Attorney, Agent, or Firm*—Young & Thompson

[57] ABSTRACT

The sharpening device for dental instruments comprises a chuck head holder having an arcuate member to one end of which the chuck head with the chuck is radially attached while the arcuate member is guided in a base of the device. The grinding head with the grinding wheel comprises a grinding head bearing which is rotatable around the mid-perpendicular of the base and includes a pivot which extends in parallel to the surface of the base and on which the grinding head turns, the latter being under the action of a tension spring in such a manner that the grinding wheel surface, which is disposed at an angle with respect to the mid-perpendicular, is pressed against the surface to be treated of the instrument. Moreover, the chucking assembly allows an essentially improved chucking of the instrument due to a thrust bolt which is actuated by an eccentric member and presses the shank of the instrument against the chuck opening. The head of the thrust bolt may be movable in order to adapt to the shape of the shank. The supports of the device are essentially simplified with respect to the prior art, and its manufacture is therefore more economical without losing the required precision.

10 Claims, 10 Drawing Sheets

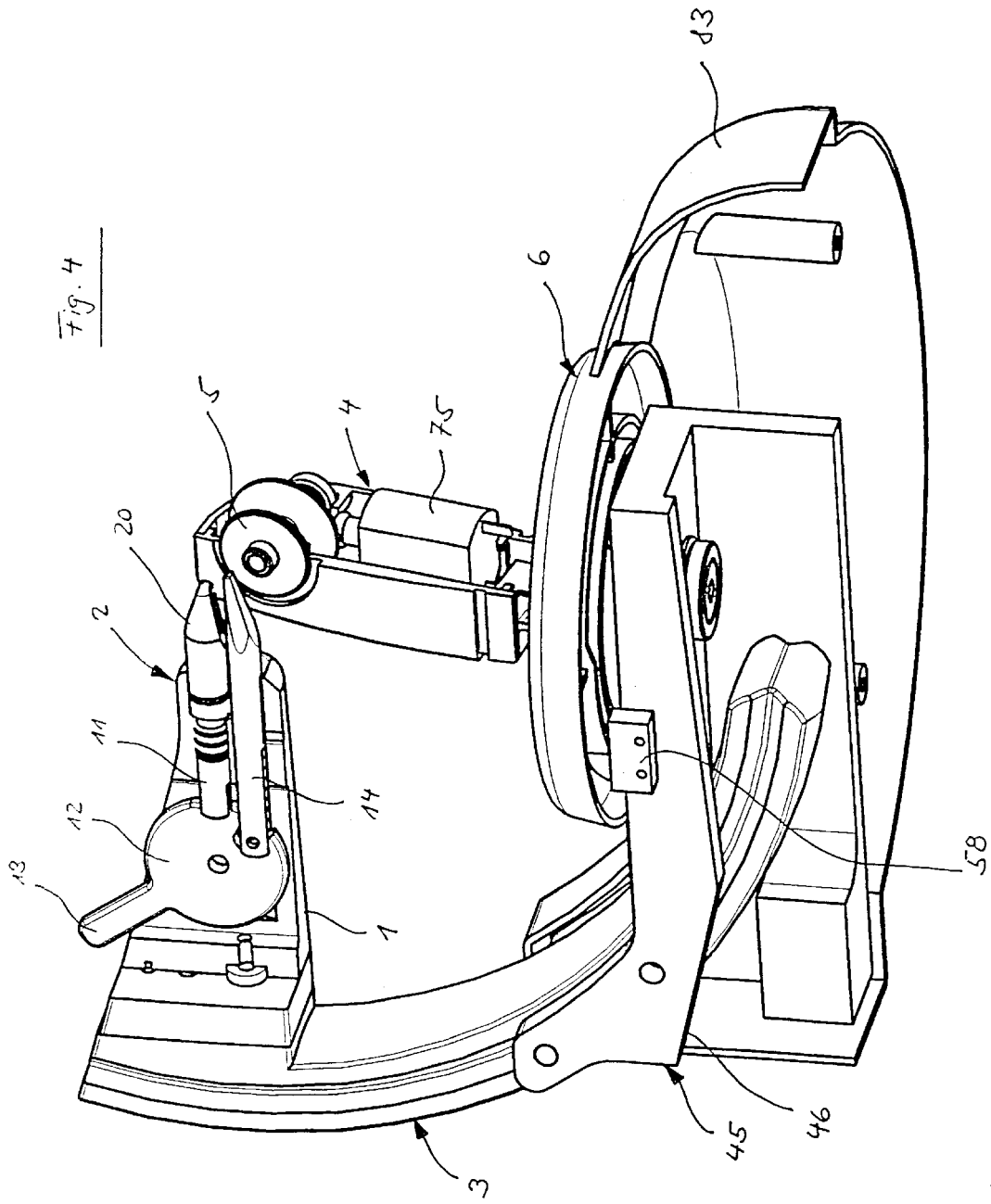

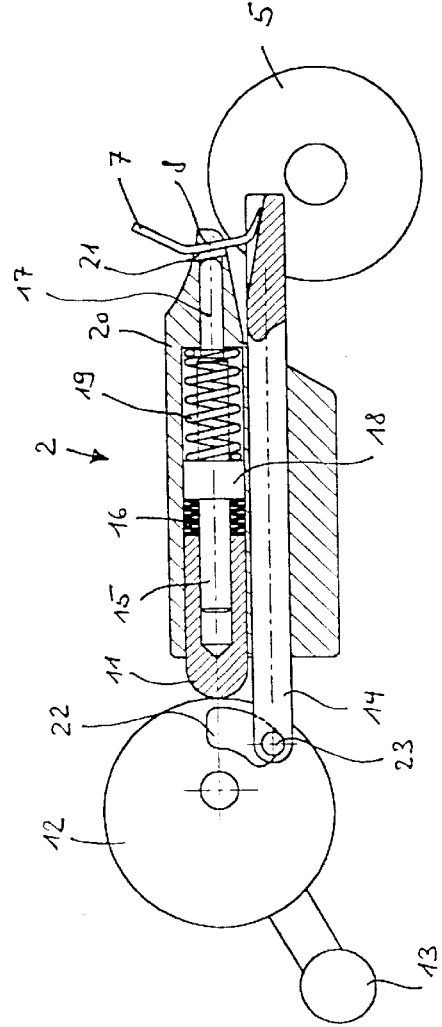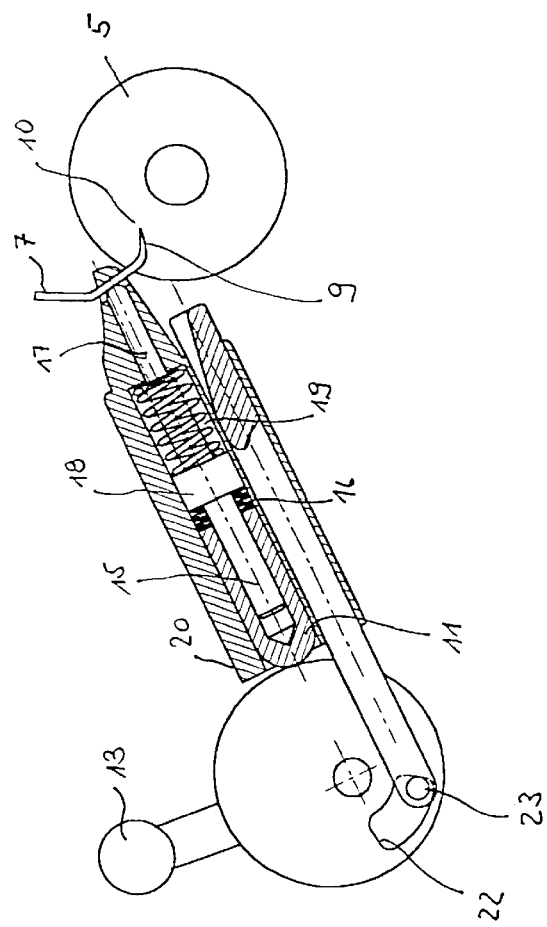

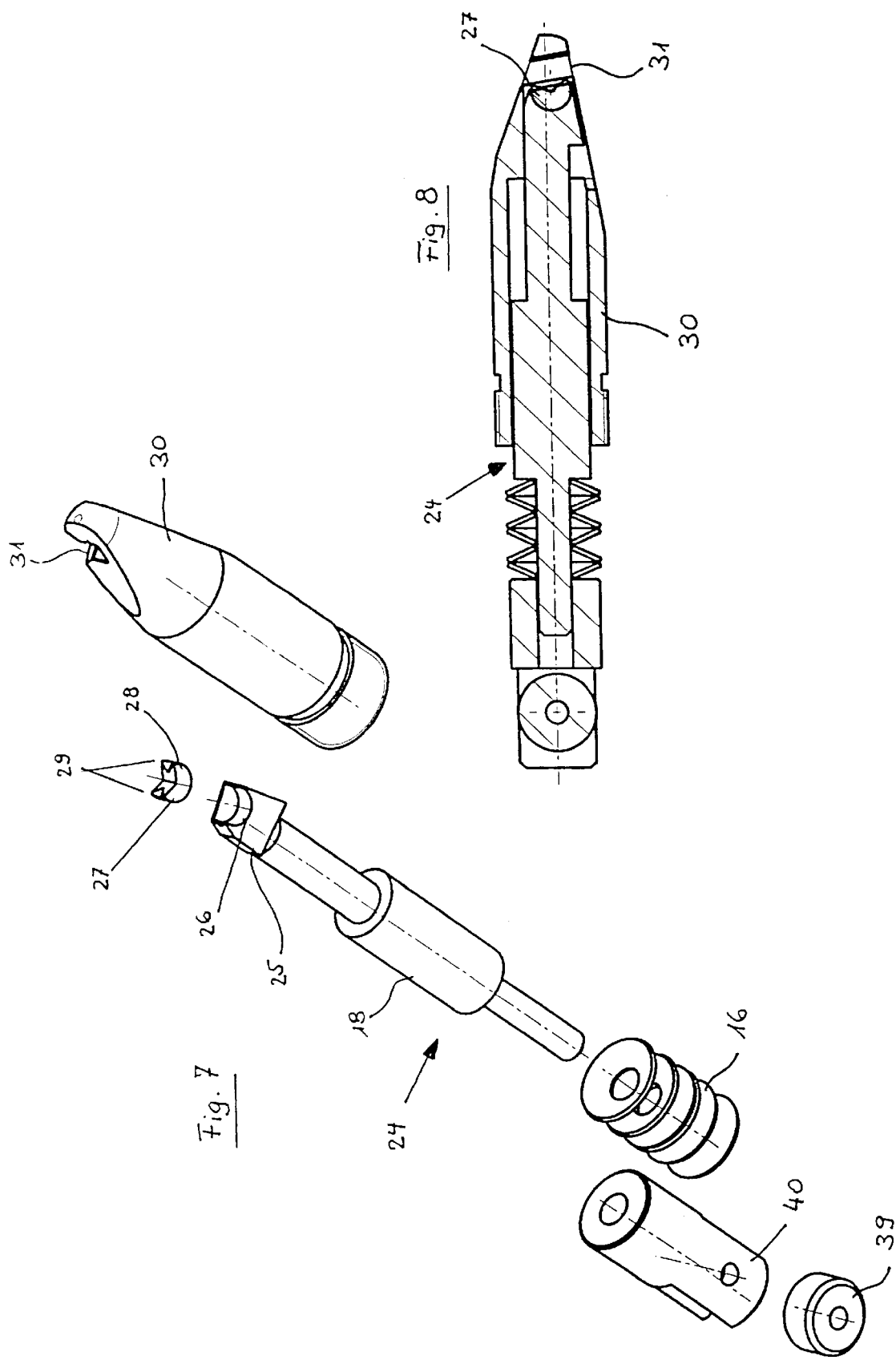

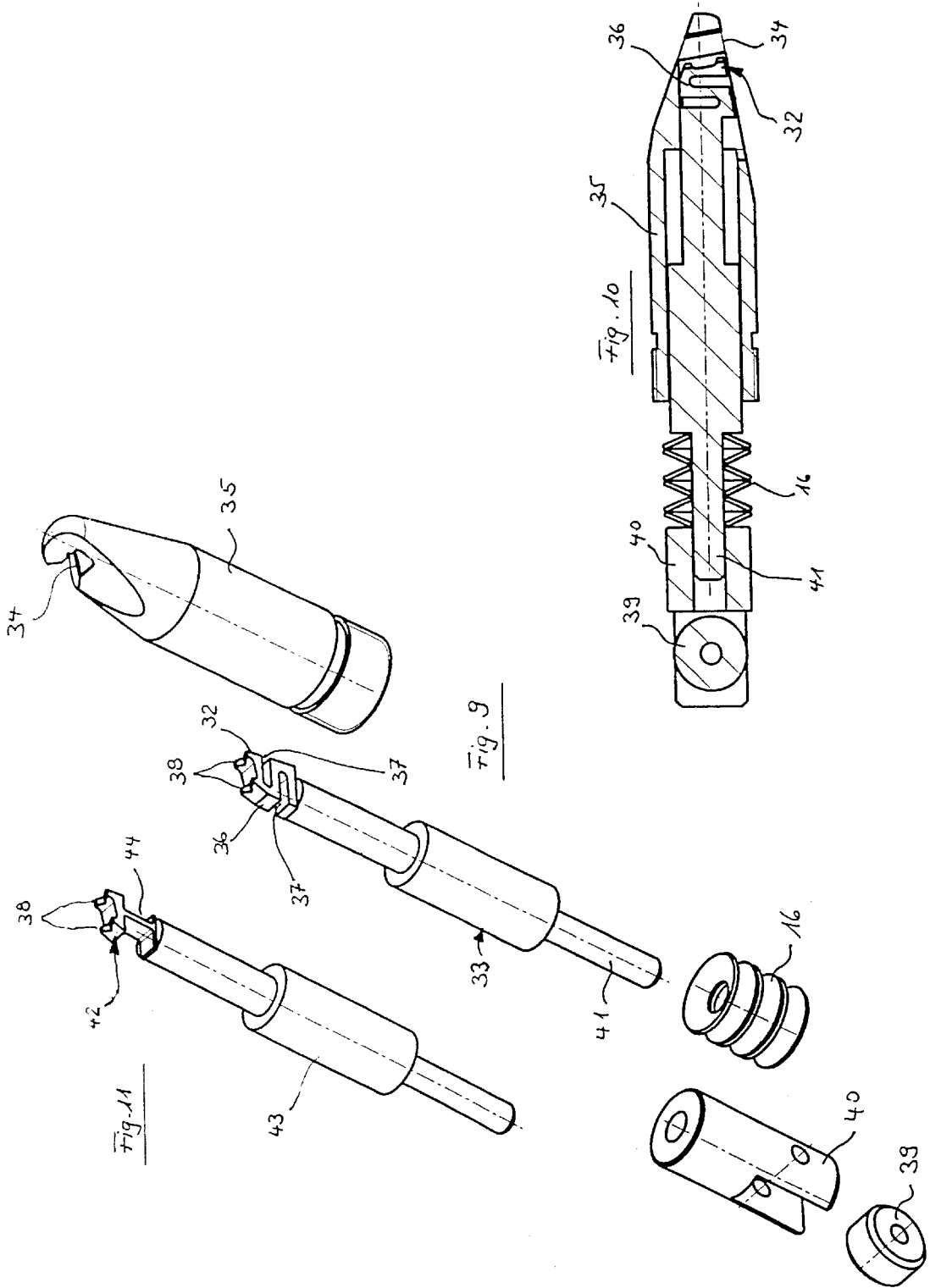

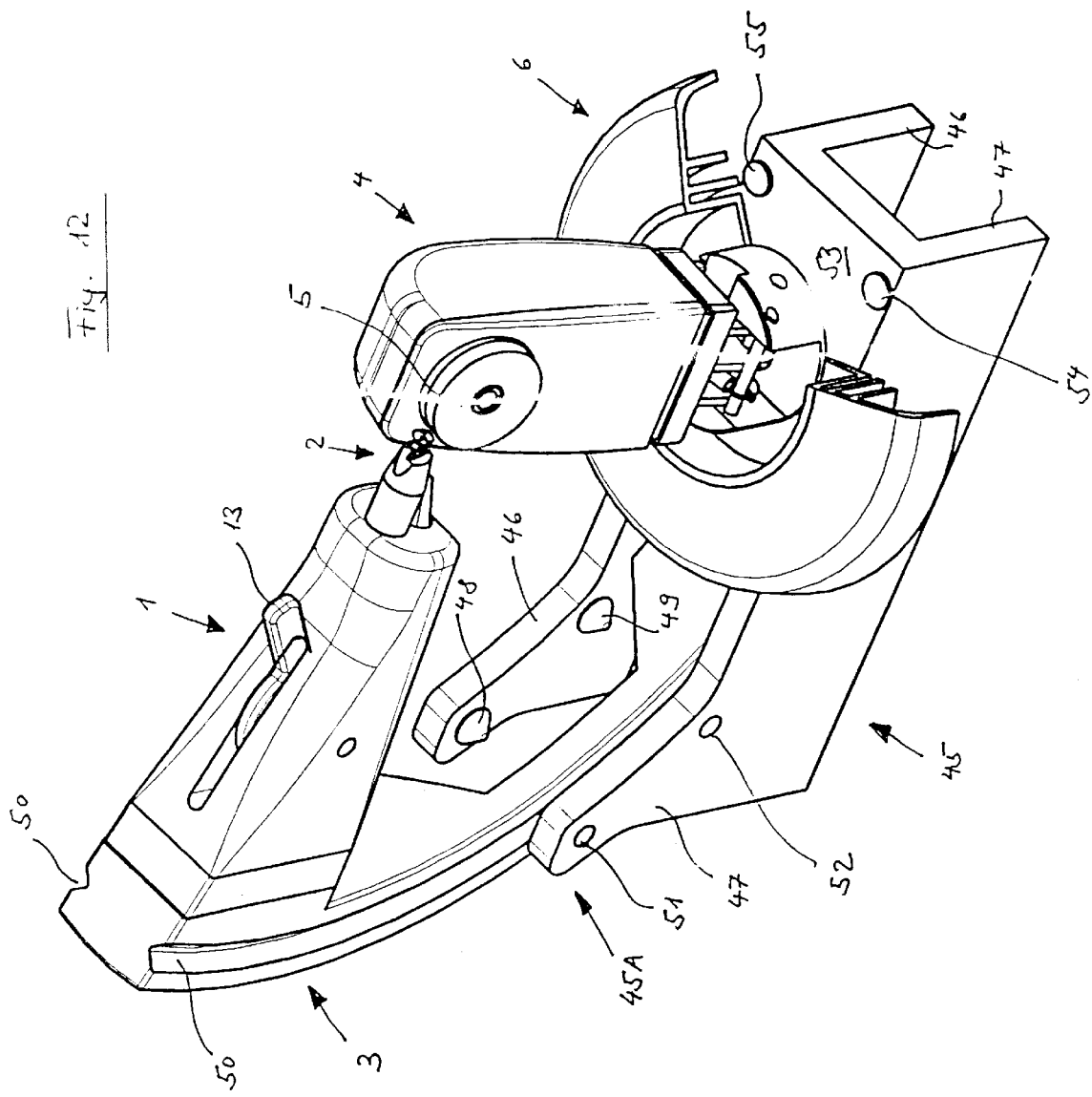

SHARPENING DEVICE FOR DENTAL INSTRUMENTS

FIELD OF THE INVENTION

The present invention relates to a device for the purpose of sharpening, grinding, or polishing dental, periodontal, or surgical instruments, comprising a holder in order to adjust the position of the chuck retaining the instrument to be treated and a grinding head bearing which is provided with means allowing to approach the surface of the grinding wheel to the surface to be treated of said instrument and which is rotatable around its perpendicular axis, as well as a base which supports said holder and said bearing. The invention further relates to a chucking assembly.

Such a device is e.g. disclosed in the European Patent Specification No. 0,307,740, an essential feature of this apparatus being the suspension of the grinding wheel on two supports which are arranged in a four-joint parallelogram connection while the suspension is rotatable around a perpendicular axis. The instrument to be treated is clamped in a chuck, and the chuck is arranged in an arcuate arm which is supported on the base of the apparatus by means of two supports while the chuck holder is pivotable around the center of the arc in order to align the surface to be sharpened.

The apparatus produced according to the cited patent distinguishes itself by great precision, simple handling, and by a wide range of applications, and it represented an important improvement over the prior art. On the base of this apparatus, it has been recognized that both the holder of the grinding wheel and the chuck holder as well as the chuck for the clamping of the sharpened instrument could be essentially simplified without losing the precision required for an exact sharpening.

From the European Specification No. 0,513,283, a device for sharpening, grinding, and polishing instruments of a similar design is known where the grinding wheel is also displaceably held in a suspension of the parallelogram type while the instrument holder is attached to two columns and linearly displaceable between the columns.

The European Patent Application No. 0,306,267 discloses a sharpening device for dental instruments where the grinding wheel is rigidly chucked at a certain angle and the instrument holder is pivotable and rotatable around its own axis on a ball joint secured by means of a wing nut. In contrast to the previously described arrangements where the grinding wheel is approached to the sharpened surface of the instrument by spring action while it is pivotable around the surface resp. the point of the instrument, both the grinding wheel and the instrument are rigidly chucked during the sharpening process, and a magnetic force acts between the grinding wheel and the instrument and the surface or the point of the instrument is pivoted with respect to the grinding wheel.

SUMMARY OF THE INVENTION

On the background of this prior art, it is a first general object of the invention to substantially simplify the holders of the instrument and thus to achieve a simplification and a cost reduction in the manufacture without impairing the required precision in the sharpening of such instruments. In particular, a first object of the invention is to simplify the retention of the grinding head, another object is to simplify the chuck holder, and still another object is to allow a better chucking of the instrument in the chuck. These objects are attained by a device wherein the chuck head holder is an arcuate member which is guided in the base, the chuck head which contains the chuck being radially fastened to one end of the chuck head holder, and its position being adjustable by pivoting the holder. Further improvements and advantages are disclosed in the dependent claims.

BRIEF DESCRIPTION OF THE DRAWINGS

The invention is explained in more detail hereinafter by means of a drawing of embodiments.

FIG. 3 shows a detail of the device of FIG. 1;

FIG. 4 shows the device of FIG. 1 with further details in a partially sectioned perspective view;

FIGS. 5 and 6 show longitudinal sections of a chucking assembly of the device of FIG. 1 in two different positions, respectively;

FIGS. 7 and 8 show an alternative embodiment of the chuck of FIG. 5;

FIGS. 9 and 10 show a second alternative embodiment of the chucks of FIGS. 5 or 7;

FIG. 11 shows an alternative embodiment of the chuck of FIG. 9;

FIG. 12 shows further details of the device of FIG. 1 in a partly sectioned perspective view;

DETAILED DESCRIPTION OF THE INVENTION

Figure 1:
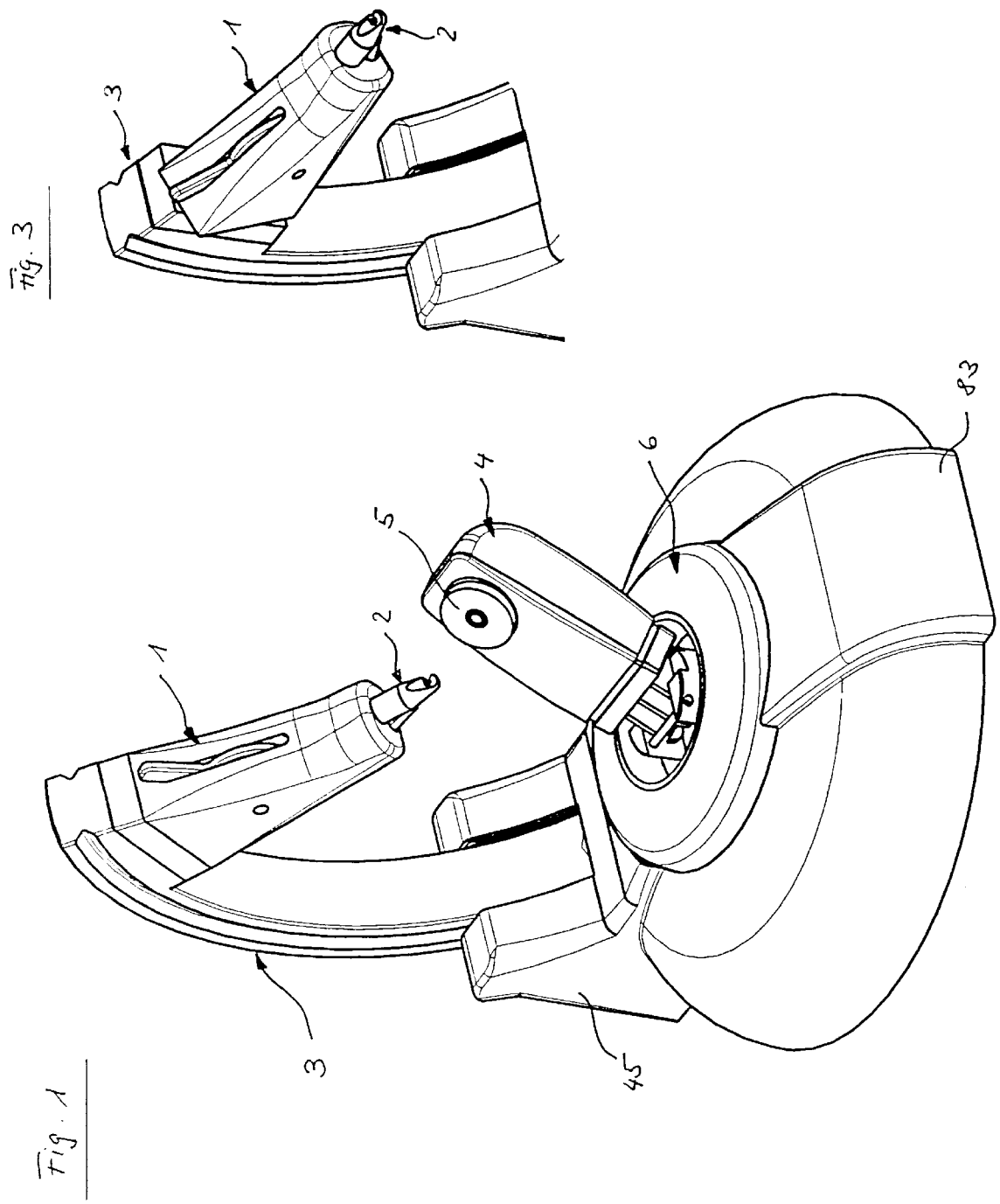
FIG. 1 shows the device of the invention in a schematical manner and in a perspective view.
Figure 2:
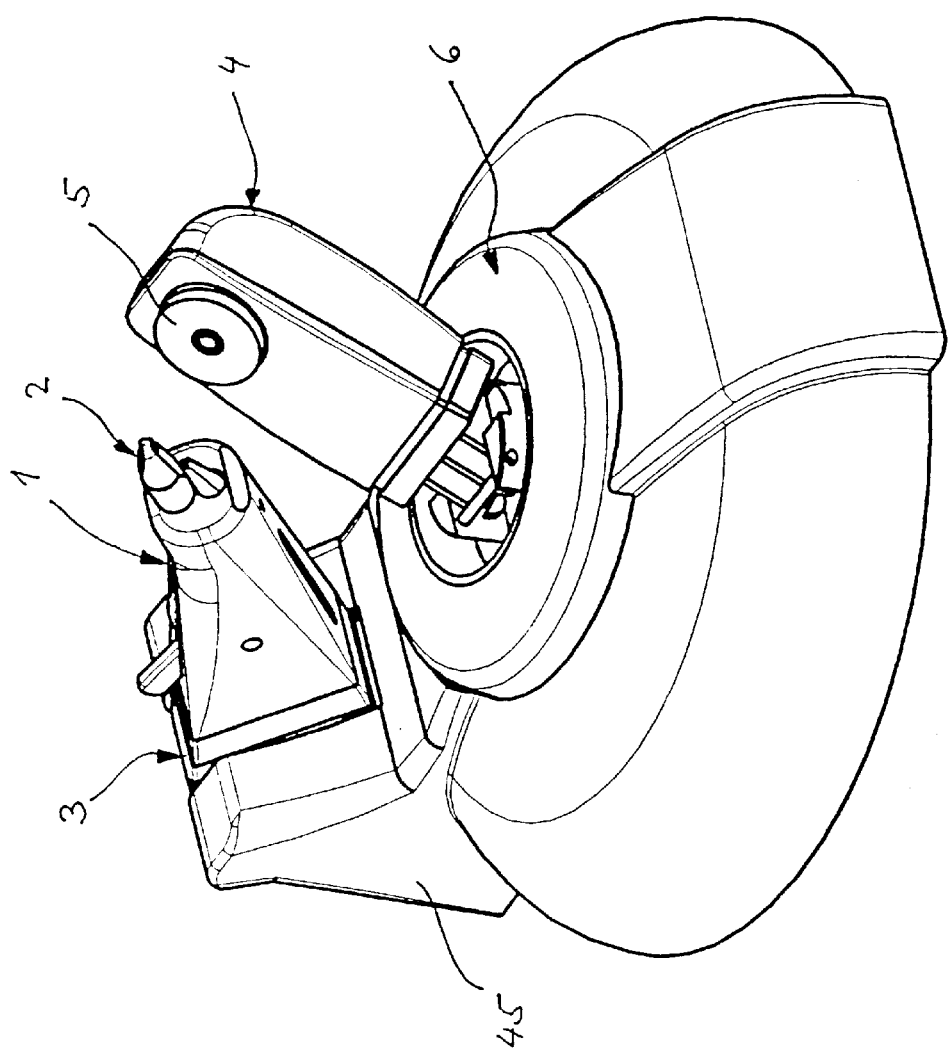
FIG. 2 shows the device of FIG. 1 in another position.

FIG. 1 shows the essential elements of the device of the invention, i.e. chuck head 1 including chuck 2 for the retention of the sharpened instrument, the chuck head being fastened to an arcuate chuck head holder 3, as well as grinding head 4 including grinding wheel 5, the grinding head being pivotably fastened to rotary plate 6. As appears in FIGS. 1 to 3, chuck head holder 3 may be turned up 30° and down 45° from the horizontal position according to FIG. 3. It is understood that the indicated values do not represent limitations but are useful values for the intended purposes.

FIG. 3 further shows that chuck head is rotatable relative to chuck head holder 3 about its central axis, the maximum rotation being 20° in each direction and the different positions being determined by snap means in the form of spring-loaded balls, for example. While this rotary movement is necessary for the sharpening of certain instrument surfaces, other instruments may require different positions and rotational angles.

The chuck is an important element of a grinding apparatus as it is to ensure a precise and firm chucking of the dental instrument. However, in many grinding apparatus of the prior art, although the grinding wheel may be chucked and aligned in some way, the dental instrument is held and guided manually and only a hand rest is possibly provided. In such apparatus, the precision of the operation of sharpening the cutting surface essentially depends on the skill of the dentist, and it is therefore not reproducible. Thus, in order to obtain reproducible and precise results, it is necessary to chuck the instrument in a precisely defined position.

FIGS. 4 to 11 show some embodiments of a chucking assembly which shall now be explained in more detail. FIGS. 5 and 6 are most suitable for the description of the chucking assembly of the invention. The figures show part of a dental instrument, e.g. a curette 7, whose first shank portion 8 behind cutting edge 9 is chucked, the point 10 of the instrument of FIG. 5 or 6 facing right, i.e. the operator.

The chucking assembly comprises a thrust bolt 15 comprising a central supporting portion 18, which runs in a chuck housing 20. On its side opposite the chucked instrument, the thrust bolt carries a thrust sleeve 11 which is actuated by a chucking member in the form of an eccentric disk with a handle 13. This eccentric disk may also be in the form of a wheel or the like. Disk springs 16 are disposed between thrust sleeve 11 and supporting portion 18 of the thrust bolt, whereas the other part of the thrust bolt, i.e. chucking portion 17, is under the action of a pressure spring 19 which rests on supporting portion 18 and on the inside of the housing. Furthermore, also within the chuck housing, a positioning bar 14 extends underneath the thrust bolt.

FIG. 5 shows the loading position, and it appears that positioning bar 14 is in the advanced position with the back of cutting edge 9 of dental instrument 7 resting thereon in order to ensure a clearly defined height adjustment in the clamping operation. The instrument is passed through chuck opening 21 in the foremost section of the chuck housing, the clamping surface of the chuck opening forming a part of the proper chuck.

When the chucking member is moved from the position of FIG. 5 to the position of FIG. 6, thrust bolt 15 is first advanced, the front end of its chuck portion 17 pressing the instrument against the clamping surface of opening 21 and thus clamping the instrument. After a short delay, which is a result of segment-shaped opening 22 of eccentric disk 12, positioning bar 14 is retracted, thus allowing an unhindered treatment of the dental instrument in any desired position.

The clamping surface of the chuck opening of the chuck according to FIGS. 5 and 6 may e.g. comprise a conical recess while the thrust bolt has a rounded end, so that a three-point rest of the instrument shank may be obtained.

In order to ensure a better three-point rest, FIGS. 7 and 8 describe an alternative embodiment where the front end of thrust bolt 24 comprises a head 25 having a semicircular recess 26 in which a rocker 27 is disposed whose semicircular back side 28 is displaceable in semicircular recess 26 and comprises two clamping corners 29 which are capable of clamping the shank of the instrument in conjunction with the clamping surface. Along with the previously described springs and the thrust sleeve, thrust bolt 24 runs in the chuck housing 30 which is provided at its front end with chuck member 31 and the clamping surface which cooperates with the thrust bolt. In FIG. 8, these elements are shown in the assembled condition in a sectional view. A precise and firm retention of the instrument is always ensured by the fact that the rocker is freely displaceable in the head of the thrust bolt.

FIG. 10 illustrates another alternative embodiment where the displaceable rocker is replaced by an elastic element 32 on thrust bolt 33 while chuck opening 34 of chuck housing 35 is essentially the same as in the previous example. In the present case, elastic element 32 consists of a plate having a respective incision 37 on both sides, thus allowing both an axial and also a certain transversal movement of the plate for best possible adaptation of clamping points 38 to the dental instrument.

In this embodiment, eccentric disk 12 of the clamping member does not actuate a thrust sleeve but a wheel 39 which is rotatably secured in a bearing element 40 and connected to rear portion 41 of thrust bolt 33. The thrust bolt is actuated by the same springs as in the previous examples, and it is illustrated in the assembled condition in the sectional view of FIG. 10.

FIG. 11 shows an alternative embodiment of FIG. 9 where the head 42 of thrust bolt 43 is provided with a plate 44 which extends in the longitudinal axis and which is so elastic that the two clamping points 38 are also capable of adapting to the shank of the dental instrument in order to ensure a safe retention in this manner. The other elements and the assembly correspond to the previous example according to FIGS. 9 and 10.

FIGS. 5, 6, 8, and 10 show clearly that the axis of the chuck opening, resp. of the clamping surface, is not perpendicular to the longitudinal axis of the chuck head but includes and angle of approx. 80° thereto.

The attachment of chuck head support 3 is illustrated in FIG. 12, in particular. The support is guided in a base 45 of U-shaped cross-section. The end 45A of the base where support 3 is guided is raised. By a swivelling motion of the chuck head support, the position of the chuck resp. of the instrument can be adjusted in order to take account of the disposition and of the configuration of the sharpened surface of a large number of different instruments.

The internal surface of the two shanks 46 and 47 of the base is provided with guiding pins 48 and 49. The upper guiding pins 48 are disposed near the ends of the shanks, and the second guiding pins 49 below the first ones. The guiding pins taper outwardly, and a respective pair of them engages in each guiding groove 50, the latter tapering inwardly and extending along the semicircular chuck head support 3, as illustrated in FIG. 12 in particular.

The raised configuration of the end of the base comprising the guiding pins and the disposition of the guiding pins allow to swivel the chuck support across the full range etween +30° up and −45° down from the horizontal direction without making the free end of the support protrude from the rotary table. The support should be guided and held with minimum play. This may e.g. be obtained if the guiding pins 51 and 52 are rigidly mounted in one shank, e.g. in shank 47, and the other two guiding pins 48 and 49 are spring-loaded.

Furthermore it is useful to lock the chuck support in certain positions, e.g. in the horizontal position and at +30° and −45°. This may e.g. be achieved by providing indentations at the corresponding positions of one of the guiding grooves where one of the two spring-loaded guiding pins may snap in, e.g. pin 48. For this purpose, the point of the other guiding pin of the same side, e.g. of guiding pin 49, must not engage in the indentations, i.e. it must be in the form of a wedge running in the guiding groove, for example. However, it is also possible to use a third pin, i.e. a catch pin which snaps in at the corresponding positions, but not the other pins. It is understood that FIG. 20 other snap-in positions may be provided as well.

It is also possible instead of the guidance by means of guiding pins running in guiding grooves to provide other bearing and guiding means of the chuck head support, e.g. bearings which are provided above and underneath the arc of the support and of which e.g. the lower ones are spring-loaded.

FIG. 12 further illustrates the manner in which rotary table 6 carrying grinding head 4 with grinding wheel 5 is rotatably mounted on base 45. The surface 53 of base 45 comprises four bearing plugs 54 whose surfaces are coated with a particularly slidable material. As shown in FIG. 12 as well, the rotary table runs on these bearing plugs via a rib 55. Rotary table 6 further comprises a peg 56, as illustrated in FIG. 13, which runs in a non-represented bearing sleeve which is fastened in a corresponding opening of the base from the underside and serves as a radial bearing of the rotary table.

Figure 13:
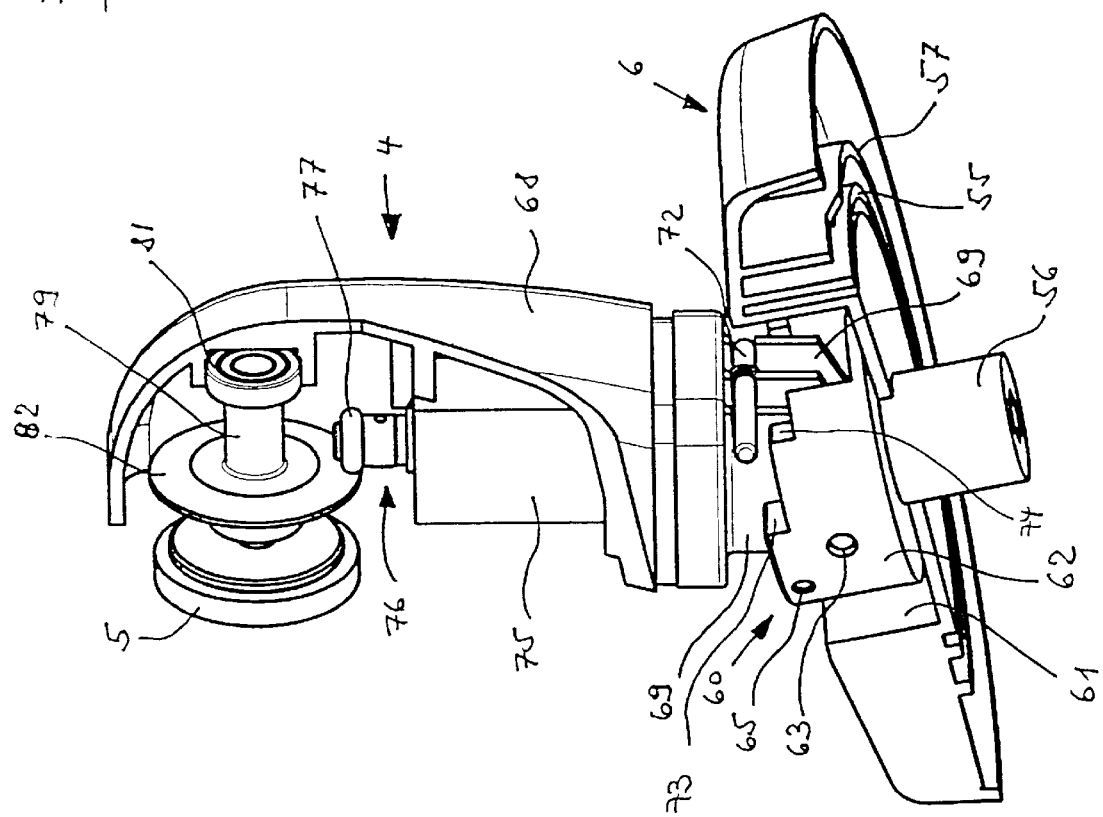
FIG. 13 shows further details of the device of FIG. 1 in a partly sectioned perspective view.

FIG. 13 further shows that sliding rib 55 is followed on the outside by another rib 57 whose height is not constant over the entire circumference and which therefore actuates a microswitch 58, see FIG. 4, in the course of the rotation of the rotary table in order to reverse the rotating direction of the grinding wheel in certain positions of the rotary table. Furthermore, the surface of the rotary table comprises a hand rest 84, see FIG. 1.

Figure 14:
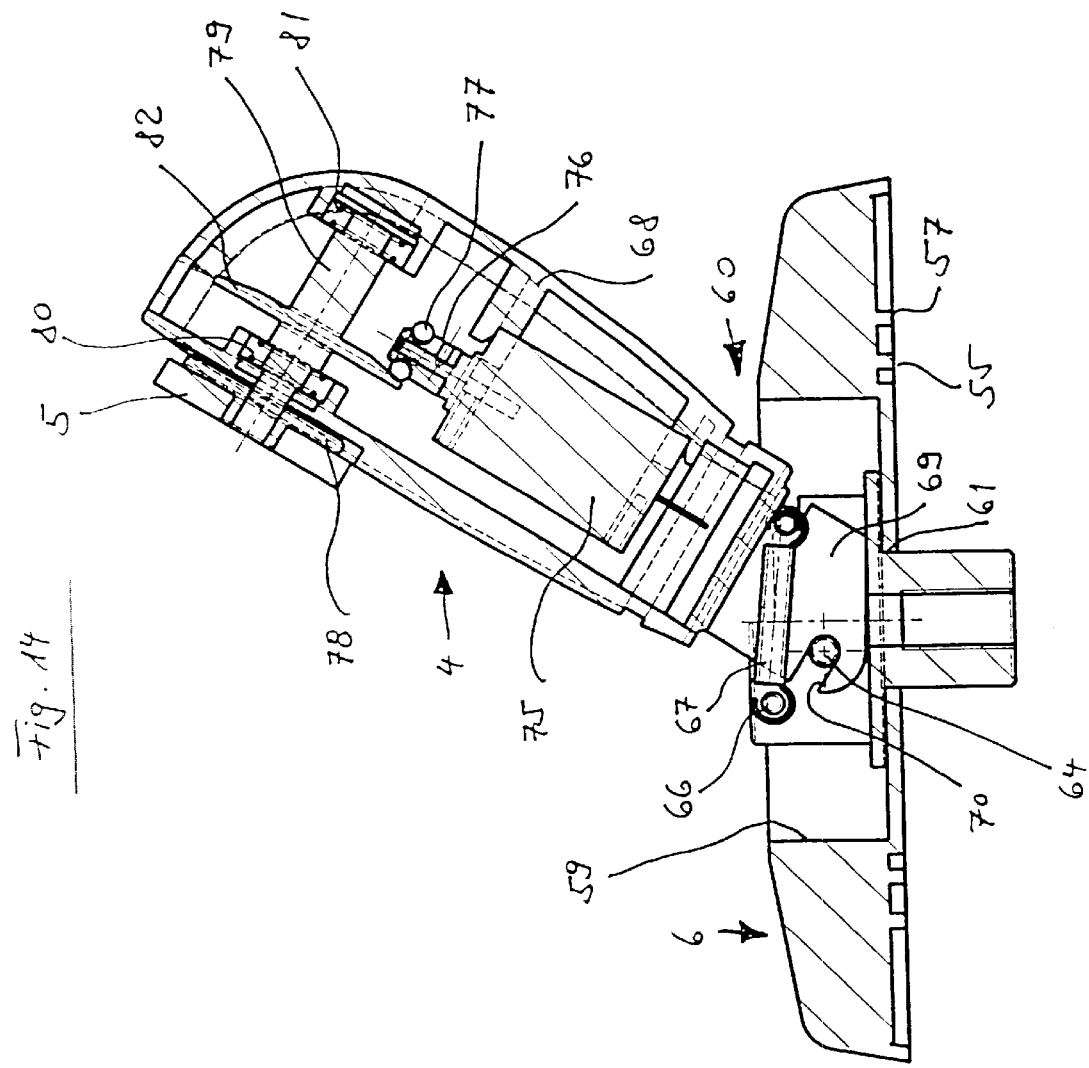
FIGS. 14 and 15 show further details of the device of the invention according to FIG. 1 in a longitudinal section.
Figure 15:
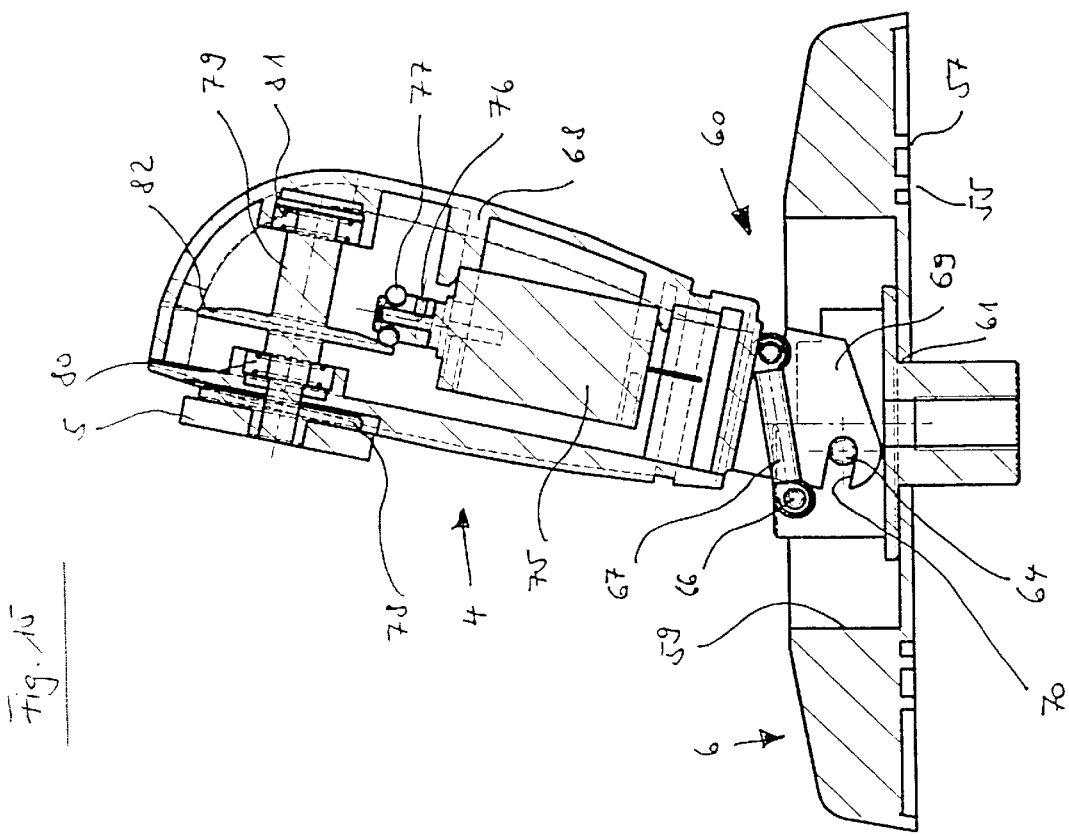

In FIGS. 13 to 15, the bearing of the grinding head, on one hand, and the drive of the grinding wheel, on the other hand, are explained in more detail. Bearing 60 of the grinding head is disposed in a central recess of rotary table 6. Grinding head bearing 60, which is made in one piece with peg 56, is secured in an opening 61 at the center of the rotary table and comprises two bearing walls 62 in each of which two openings are provided, the lower openings 63 being intended to receive axle 64 which serves as a pivot of the grinding head. The upper openings 65 serve to receive a pin 66 to which a tension spring 67 is secured.

Grinding head 4 comprises a grinding head casing 68, grinding wheel 5 being disposed in the upper section thereof while the drive of the grinding wheel is disposed inside the casing. At its lower end, grinding head casing 68 comprises two bearing members 69 whose plane extends in parallel to the axis of the grinding wheel and which are each provided with a respective recess 70 on the grinding wheel side in order to engage behind pivot 64, as shown in FIGS. 14 and 15. Near the grinding head casing, the two bearing members 69 are each provided with a second recess 71 which serves to receive a pin 72 to which tension spring 67 is secured. An appropriate dimensioning of the tension spring allows to establish and maintain the desired constant grinding pressure of the grinding wheel.

FIG. 3 shows that the sides of bearing walls 62 opposite the grinding wheel comprise two steps 73 and 74 in which pin 72 of the tension spring can engage, the pin being engaged in the lower step 74 in the rest position, see FIG. 14, and in the upper step 73 in the active position. In this active position, the plane of grinding wheel surface 5A is inclined about 15° with respect to the mid-perpendicular M.

FIGS. 13 to 15 further illustrate the drive of the grinding wheel. It is advantageous to use a wheel and disk drive, whose construction is very simple and whose operation noise is relatively low. On its output shaft, electric motor 75 is provided with a friction wheel 76 which is equipped e.g. with a rubber-elastic ring or with an O-ring 77. Grinding wheel support 78 comprises an axle 79 which is supported in the grinding head casing perpendicularly to the longitudinal axis thereof and about perpendicularly to the output shaft of the electric motor at two points 80 and 81. A friction disk 82 is secured to axle 79 which cooperates with friction wheel 76. The desired rotational speed of the grinding wheel is determined by the speed of the electric motor and by the multiplication resp. reduction ratio between the friction wheel and the friction disk.

The grinding wheel may be fastened to the grinding wheel support in different ways. Instead of using a friction wheel and a friction disk, it is also possible to use an angular gear, e.g. an angular gear which is mounted on the output shaft of the electric motor and which acts on an angular gear on the grinding wheel axle, in which case a 90° gear may be used.

Furthermore it is possible instead of the described suspension of the grinding head to provide a rotary axle on which the rotary table turns and which comprises a pivot extending in parallel to the hand rest, as well as a tension spring which is secured to the rotary table, on one hand, and to the grinding head, on the other hand, in order to maintain the latter in a determined angular position.

I claim:

1. A device for the treatment of dental or surgical instruments, comprising:
   holder for adjusting a position of a chuck retaining an instrument to be treated,
   a grinding head bearing which is provided with means for allowing a grinding wheel surface to approach a surface of the instrument to be treated and which is rotatable around a perpendicular axis, and
   a base carrying said holder and said bearing,
   wherein said holder is an arcuate member which is guided in said base, a chuck head which contains the chuck being radially fastened to one end of said holder, and its position being adjustable by pivoting said holder.

2. The device of claim 1, further comprising two pairs of guiding pins which are disposed on inner sides of shanks of said base and which each engage in a respective guiding groove in sides of said holder.

3. The device of claim 2, wherein a respective one of said guiding pins is disposed near an end of each said shank of said base and a respective one of said guiding pins is disposed therebelow, the guiding pins tapering outwardly and the guiding grooves tapering inwardly.

4. The device of claim 2, wherein one pair of said guiding pins is fixed in one of said shanks while another pair of said guiding pins is spring-loaded in the other of said shanks.

5. The device of claim 1, further comprising an electric motor driving the grinding wheel surface and connected to an axle of the grinding wheel surface by an angular gear.

6. The device of claim 5, wherein said electric motor is disposed in a longitudinal axis of the grinding head bearing and the axle of the grinding wheel surface is perpendicular thereto.

7. The device of claim 5, wherein said angular gear is one of a wheel and disk drive and a gearwheel drive.

8. A device for the treatment of dental or surgical instruments, comprising:
   holder for adjusting a position of a chuck that holds an instrument to be treated;
   a grinding head bearing which is provided with means for allowing a grinding wheel surface to approach a surface of the instrument to be treated and which is rotatable around a perpendicular axis, and
   a base carrying said holder and said bearing, and
   wherein said grinding head bearing is pivotably disposed on a rotary table which is rotatable around the perpendicular axis, said rotary table containing a pivot which extends in parallel to a surface of said base and on which the grinding head bearing is hinged, the latter being under the action of a tension spring in such a manner that the grinding wheel surface, which is disposed at an angle with respect to the perpendicular axis, is pressed against the surface of the instrument to be treated.

9. The device of claim 8, wherein the grinding head bearing in the rotary table includes two bearing walls opposite each other which comprise a respective opening receiving said pivot and an opening receiving a pin of said tension spring, as well as two steps engaging another pin of said tension spring in an active and in a rest position, the grinding head bearing turning on said pivot.

10. The device of claim 2, wherein the surface of said base is provided with sliding plugs and the underside of said rotary table comprises a circular sliding rib which corresponds to said sliding plugs.

* * * * *

UNITED STATES PATENT AND TRADEMARK OFFICE
CERTIFICATE OF CORRECTION

PATENT NO. : 6,142,856
DATED : November 7, 2000
INVENTOR(S) : Ludwig Römhild

It is certified that error appears in the above-identified patent and that said Letters Patent is hereby corrected as shown below:

Column 6,
Line 62, change "claim 2" to -- claim 8, -- .

Signed and Sealed this

Eleventh Day of September, 2001

Attest:

*Nicholas P. Godici*

NICHOLAS P. GODICI
*Attesting Officer*    *Acting Director of the United States Patent and Trademark Office*